United States Patent [19]

Berntsson et al.

[11] 4,264,611
[45] Apr. 28, 1981

[54] 2,6-DIMETHYL-4-2,3-DISUBSTITUTED PHENYL-1,4-DIHYDRO-PYRIDINE-3,5-DICARBOXYLIC ACID-3,5-ASYMMETRIC DIESTERS HAVING HYPOTENSIVE PROPERTIES, AS WELL AS METHOD FOR TREATING HYPERTENSIVE CONDITIONS AND PHARMACEUTICAL PREPARATIONS CONTAINING SAME

[75] Inventors: Peder B. Berntsson, Mölndal, Stig Å. I. Carlsson, Mölnlycke, Jan Ö. Gaarder, Göteborg, Bengt R. Ljung, all of Sweden

[73] Assignee: Aktiebolaget Hassle, Mölndal, Sweden

[21] Appl. No.: 50,083

[22] Filed: Jun. 19, 1979

[30] Foreign Application Priority Data

Jun. 30, 1978 [SE] Sweden .................. 7807404

[51] Int. Cl.³ .................. C07D 213/55; A61K 31/455
[52] U.S. Cl. .................. 424/266; 546/321
[58] Field of Search .................. 546/321; 424/266

[56] References Cited

U.S. PATENT DOCUMENTS

| | | | |
|---|---|---|---|
| 3,441,648 | 4/1969 | Loev et al. | 546/321 |
| 3,488,359 | 1/1970 | Bossert et al. | 546/321 |
| 3,799,936 | 5/1974 | Meyer et al. | 546/321 |

*Primary Examiner*—Alan L. Rotman
*Attorney, Agent, or Firm*—Brumbaugh, Graves, Donohue & Raymond

[57] ABSTRACT

The present invention relates to new compounds having antihypertensive effect, which compounds are of the formula I,

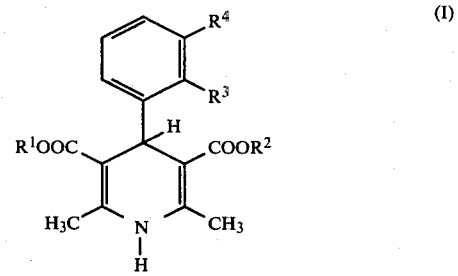

wherein $R^1$ is selected from the group consisting of —$CH_3$, —$C_2H_5$, —$CH_2CH_2OCH_3$, and —$CH_2CH_2OC_2H_5$, and $R^2$ is selected from the group consisting of —$C_2H_5$, —$CH(CH_3)_2$, —$C(CH_3)_3$, —$CH(CH_3)CH_2OCH_3$, $C(CH_3)_2CH_2OCH_3$, and —$CH_2C(CH_3)=CH_2$, whereby $R^1$ and $R^2$ are not the same, $R^3$ is selected from the group consisting of chloro, and $R^4$ is selected from the group consisting of chloro, and methyl, a method for lowering the blood pressure in mammals including man using said compounds, and pharmaceutical preparations containing said compounds.

30 Claims, No Drawings

2,6-DIMETHYL-4-2,3-DISUBSTITUTED PHENYL-1,4-DIHYDRO-PYRIDINE-3,5-DICARBOXYLIC ACID-3,5-ASYMMETRIC DIESTERS HAVING HYPOTENSIVE PROPERTIES, AS WELL AS METHOD FOR TREATING HYPERTENSIVE CONDITIONS AND PHARMACEUTICAL PREPARATIONS CONTAINING SAME

DESCRIPTION

TECHNICAL FIELD

The present invention relates to new compounds having valuable antihypertensive properties, process for their preparation, method for lowering blood pressure in mammals including man, and pharmaceutical preparations containing said compounds.

The object of the present invention is to obtain new antihypertensive agents, which lower blood pressure in the peripheral vessels in lower doses than they lower blood pressure in the heart vessels, by selective dilation of peripheral blood vessels.

BACKGROUND OF THE INVENTION

Compounds of the formula

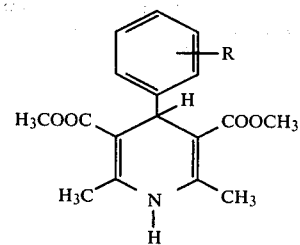

wherein R is nitro or trifluoromethyl in 2 or 3-position are known to possess cerebral vasodilating effect, effect against angina pectoris or blood pressure lowering effect.

Agents which relax vascular smooth muscle may be used for treatment of arterial hypertension since such patients suffer from elevated peripheral resistance to blood flow. Compounds which interfere with vascular smooth muscle activity have been used clinically for several years. However, their usefulness has often been limited due to insufficient efficacy and/or due to adverse effects. Side effects (outside the cardiovascular system) have often been connected with properties of the agent not relevant to the smooth muscle relaxant effect. Sometimes the vasodilating agents have also exerted a negative effect on the contractility of the heart.

It appears that the development of specific smooth muscle relaxants devoid of adverse effects, can offer a therapeutic advantage in arterial hypertension and for treatment of ischaemic heart disease and of the acutely failing heart. Further more, such agents can also be useful in treatment of other conditions with excessive activation of smooth muscle of the visceral type.

DISCLOSURE OF THE INVENTION

It has now surprisingly been shown that the compounds of the formula I

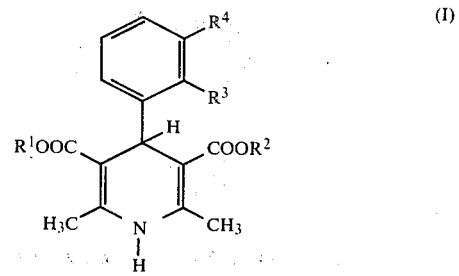

wherein $R^1$ is selected from the group consisting of $-CH_3$, $-C_2H_5$, $-CH_2CH_2OCH_3$ and $-CH_2CH_2OC_2H_5$ and $R^2$ is selected from the group consisting of $-C_2H_5$, $-CH(CH_3)_2$, $-C(CH_3)_3$, $-CH(CH_3)CH_2OCH_3$, $-C(CH_3)_2CH_2OCH_3$, and $-CH_2C(CH_3)=CH_2$, whereby $R^1$ and $R^2$ are not the same, $R^3$ is chloro, and $R^4$ is selected from the group consisting of chloro, and methyl, possess a specific muscle relaxing effect related to the peripheral vascular system whereby the compounds are devoid of adverse effects.

Specific preferred compounds of the invention are:

(1) 2,6-dimethyl-4-(2,3-dichlorophenyl)-1,4-dihydropyridine-3,5-dicarboxylic acid-3-methylester-5-ethylester;

(2) 2,6-dimethyl-4-(2,3-dichlorophenyl)-1,4-dihydropyridine-3,5-dicarboxylic acid-3-ethylester-5-(2-methoxyethylester)

(3) 2,6-dimethyl-4-(2,3-dichlorophenyl)-1,4-dihydropyridine-3,5-dicarboxylic acid-3-methylester-5-isopropylester (4) 2,6-dimethyl-4-(2,3-dichlorophenyl)-1,4-dihydropyridine-3,5-dicarboxylic acid-3-methyl-5-tert.butylester (5) 2,6-dimethyl-4-(2,3-dichlorophenyl)1,4-dihydropyridine-3,5-dicarboxylic acid-3-methylester-5-(2-methoxy-1-methylethylester)

(6) 2,6-dimethyl-4-(2,3-dichlorophenyl)-1,4-dihydropyridine-3,5-dicarboxylic acid-3-(2-methoxyethyl)ester-5-isopropylester (7) 2,6-dimethyl-4-(2,3-dichlorophenyl)-1,4-dihydropyridine-3,5-dicarboxylic acid-3-(2-ethoxyethyl)ester-5-ethylester (8) 2,6-dimethyl-4-(2,3-dichlorophenyl)-1,4-dihydropyridine-3,5-dicarboxylic acid-3-methylester-5-(2-methoxy-1,1-dimethylethyl)ester (9) 2,6-dimethyl-4-(2,3-dichlorophenyl)-1,4-dihydropyridine-3,5-dicarboxylic acid-3-methylester-5-(2-methyl)-allylester

(10) 2,6-dimethyl-4-(2-chloro-3-methylphenyl)-1,4-dihydropyridine-3,5-dicarboxylic acid-3-methylester-5-ethylester The substances are intended to be administered orally or parenterally for acute and chronic treatment of above mentioned cardiovascular disorders.

The biological effects of the new compounds have been tested, and the different tests carried out will be shown and explained below.

The new compounds are obtained according to methods known per se.

Thus, ($a^1$) a compound of formula IIa

 (IIa)

wherein $R^1$, $R^3$ and $R^4$ have the meanings given above is reacted with a compound of formula IIIa

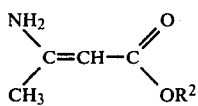 (IIIa)

(wherein $R^2$ has the meaning given above to give a compound of formula I, or ($a^2$) a compound of formula IIb

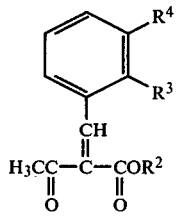 (IIb)

wherein $R^2$, $R^3$ and $R^4$ have the meanings given above is reacted with a compound of formula IIIb

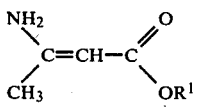 (IIIb)

wherein $R^1$ has the meaning given above, to the formation of a compound of formula I; or ($b^1$) a compound of formula IV

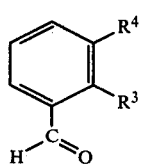 (IV)

wherein $R^3$, and $R^4$ have the meanings given above is reacted with the compounds of formulas Va and IIIa

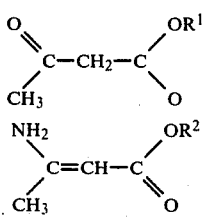

(Va)

(IIIa)

wherein $R^1$, and $R^2$ have the meanings given above to the formation of a compound of formula I, or ($b^2$) a compound of formula IV above wherein $R^3$, and $R^4$ have the meanings given above is reacted with the compounds of formulas Vb and VIb

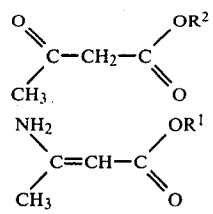

(Vb)

(VIb)

wherein $R^1$ and $R^2$ have the meanings given above, to the formation of a compound of formula I; or ($c^1$) a compound of formula IIa wherein $R^1$, $R^3$ and $R^4$ have the meanings given above is reacted with a compound of the formula VIa

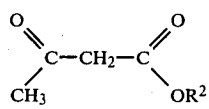 (VIa)

wherein $R^2$ has the meaning given above in the presence of ammonia, to the formation of a compound of the formula I, or ($c^2$) a compound of formula IIb wherein $R^2$, $R^3$, and $R^4$ have the meanings given above is reacted with a compound of formula VIb

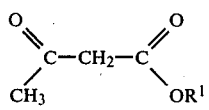 (VIb)

wherein $R^1$ has the meaning given above, in the presence of ammonia, to the formation of a compound of the formula I; or (d) a compound of formula IV above, wherein $R^3$, and $R^4$ have the meanings given above, is reacted with the compounds of the formulas Va and Vb above, wherein $R^1$ and $R^2$ have the meanings given above, in the presence of ammonia, to the formation of a compound of the formula I.

The invention also relates to any embodiment of the process of which one starts from any compound obtained as an intermediate in any process step and one carries out the lacking process step, or one breaks off the process at any step, or at which one forms a starting material under the reaction conditions, or at which a reaction component possibly in the form of its salt is present.

The new compounds may, depending on the choice of starting materials and process, be present as optical antipodes or racemate, or, if they contain at least two asymmetric carbon atoms, be present as an isomer mixture (racemate mixture).

The isomer mixtures (racemate mixtures) obtained may, depending on physical-chemical differences of the components, be separated into the two stereoisomeric (diastereomeric) pure racemates e.g. by means of chromatography and/or fractional crystallization.

The racemates obtained can be separated according to known methods, e.g., by means of recrystallization from an optically active solvent, by means of microorganisms, or by a reaction with optically active acids forming salts of the compound, and separating the salts thus obtained, e.g. by means of the different solubility of the diastereomeric salts, from which the antipodes may be set free by the action of a suitable agent. Suitably usable optically active acids are e.g. the L- and D-forms of tartaric aicd, di-o-tolyltartaric acid, malic acid, mandelic acid, camphorsulfonic acid or quinic acid. Preferably the more active part of the two antipodes is isolated.

Suitably such starting materials are used for carrying out the reactions of the invention, which material leads to groups of end products preferably desired and particularly to the specifically described and preferred end products.

The starting materials are known or may, if they are novel, be obtained according to processes known per se.

In clinical use the compounds of the invention are usually administered orally, or rectally in the form of a pharmaceutical preparation, which contains the active component as free base in combination with a pharmaceutically acceptable carrier.

Thus the mentioning of the new compounds of the invention is here related to the free amine base even if the compounds are generally or specifically described, provided that the context in which such expressions are used, e.g., in the examples, with this broad meaning should not correspond. The carrier may be a solid, semisolid or liquid diluent or a capsule. These pharmaceutical preparations are a further object of the invention. Usually the amount of active compound is between 0.1 and 99% by weight of the preparation, suitably between 0.5 and 20% by weight in preparations for injection and between 2 and 50% by weight in preparations for oral administration. In the preparation of pharmaceutical preparations containing a compound of the present invention in the form of dosage units for oral administration the compound elected may be mixed with a solid, pulverulent carrier, as e.g., with lactose, saccharose, sorbitol, mannitol, starch, such as potatoe starch, corn starch, amylopectin, cellulose derivatives or gelatine, as well as with an antifriction agent such as magnesium stearate, calcium stearate, polyethyleneglycol waxes or the like, and be pressed into tablets. If coated tablets are wanted, the above prepared core may be coated with concentrated solution of sugar, which solution may contain, e.g., gum arabicum, gelatine, talc, titandioxide or the like. Furthermore, the tablets may be coated with a laquer dissolved in an easily volatile organic solvent or mixture of solvents. To this coating a dye may be added in order to easily distinguish between tablets with different active compounds or with different amounts of the active compound present.

In the preparation of soft gelatine capsules (pearl-shaped, closed capsules), which consist of gelatine and, e.g., glycerine, or in the preparation of similar closed capsules, the active compound is mixed with a vegetable oil. Hard gelatine capsules may contain granules of the active compound in combination with a solid, pulverulent carrier as loactose, saccharose, sorbitol, mannitol, starch (as, e.g., potatoe starch, corn starch or amylopectin), cellulose derivatives or gelatine.

Dosage units for rectal administration may be prepared in the form of suppositories, which contain the active substance in a mixture with a neutral fat base, or they may be prepared in the form of gelatine-rectal capsules which contain the active substance in a mixture with a vegetable oil or paraffin oil. Liquid preparations for oral administration may be present in the form of sirups or suspensions, e.g. solutions containing from about 0.2% by weight to about 20% by weight of the active substance described, glycerol and propylene glycol. If desired, such liquid preparations may contain colouring agents, flavouring agents, saccharine and carboxymethylcellulose as a thickening agent.

The preparation of pharmaceutical tablets for peroral use is carried out in accordance with the following method:

The solid substances included are ground or sieved to a certain particle size. The binding agent is homogenized and suspended in a certain amount of solvent. The therapeutic compound and necessary auxiliary agents are mixed with continuous and constant mixing with the binding agent solution and are moistened so that the solution is uniformly divided in the mass without overmoistening any parts. The amount of solvent is usually so adapted that the mass obtains a consistency reminiscent of wet snow. The moistening of the pulverulent mixture with the binding agent solution causes the particles to gather together slightly to aggregates and the real granulating process is carried out in such a way that the mass is pressed through a sieve in the form of a net of stainless steel having a mesh size of about 1 mm. The mass is then placed in thin layers on a tray to be dried in a drying cabinet. This drying takes place during 10 hours and has to be standardized carefully as the damp degree of the granulate is of outmost importance for the following process and for the feature of the tablets. Drying in a fluid bed may possibly be used. In this case the mass is not put on a tray but is poured into a container having a net bottom. After the drying step the granules are sieved so that the particle size wanted is obtained. Under certain circumstances powder has to be removed.

To the so called final mixture, disintegrating, antifriction agents and antiadhesive agents are added. After this mixture the mass shall have its right composition for the tabletting step.

The cleaned tablet punching machine is provided with a certain set of punches and dies, whereupon the suitable adjustment for the weight of the tablets and the degree of compression is tested out. The weight of the tablet is decisive for the size of the dose in each tablet and is calculated starting from the amount of therapeutic agent in the granules. The degree of compression affects the size of the tablet, its strength and its ability to disintegrate in water. Especially with regard to the two later properties the choice of compression pressure (0.5 to 5 ton) means something of a compromise. When the right adjustment is set, the preparation of tablets is started and is carried out with a rate of 20,000 to 200,000 tablets per hour. The pressing of the tablets requires different times and depends on the size of the batch.

The tablets are freed from adhering pulver in a specific apparatus and are then stored in closed packages until they are delivered.

Many tablets, especially those which are rough or bitter, are coated with a coating. This means that they are coated with a layer of sugar or some other suitable coating. The tablets are usually packed by machines having an electronic counting device. The different types of packages consist of glass or plastic gallipots but also boxes, tubes and specific dosage adapted packages.

The daily dose of the active substance varies and is dependent on the type of administration, but as a general rule it is 100 to 1000 mg/day of active substance at peroral administration.

BEST MODE OF CARRYING OUT THE INVENTION

The following illustrates the principle and the adaption of invention, however, without being limited thereto. Temperature is given in degree Celsius.

EXAMPLE 1 (method a[1], a[2])

Preparation of 2,6-dimethyl-4-(2,3-dichlorophenyl)-1,4-dihydropyridine-3,5-dicarboxylic acid-3-methylester-5-ethylester 2.87 g of 2,3-dichlorobenzylideneacetylacetic acid-methylester and 1.3 g of 3-aminocrotonic acid ethylester were dissolved in 10 mls of t.-butanol. The reaction mixture was allowed to stand at ambient temperature for 4 days, whereupon the t.-butanol was evaporated and the residue was dissolved and was stirred with a small amount of isopropylether, whereby the compound crystallized. After recrystallization from isopropylether pure 2,6-dimethyl-4-(2,3-dichlorophenyl)-1,4-dihydropyridine-3,5-dicarboxylic acid-3-methylester-5-ethylester was obtained. M.p. 145° C. Yield 75%.

EXAMPLE 2 (method b[1], b[2])

Preparation of 2,6-dimethyl-4-(2,3-dichlorophenyl)-1,4-dihydropyridine-3,5-dicarboxylic acid-3-ethylester-5-(2-methoxyethyl)ester 4.4 g of 2,3-dichlorobenzaldehyde, 3,2 g of 3-aminocrotonic acid ethylester, 4.0 g acetylacetic acid-2-methoxyethylester and 25 mls of ethanol were refluxed over night. The reaction mixture was poured out onto icewater, whereby the compound crystallized. After filtration recrystallization was carried out from ethanol, whereby pure 2,6-dimethyl-4-(2,3-dichlorophenyl)-1,4-dihydropyridine-3,51-dicarboxylic acid-3-ethylester-5-(2-methoxyethyl)ester was obtained. M.p. 139° C. Yield 36%.

EXAMPLES 3–10

The compounds of table 1 below were prepared in accordance with Examples 1 and 2 above.

TABLE 1

| Ex No. | R[1] | R[2] | R[3] | R[4] | Prep acc to Ex | Mp °C. | Yield % |
|---|---|---|---|---|---|---|---|
| 3 | —CH$_3$ | —CH(CH$_3$)$_2$ | Cl | Cl | 2 | 148 | 47 |
| 4 | —CH$_3$ | —C(CH$_3$)$_3$ | Cl | Cl | 1 | 156 | 32 |
| 5 | —CH$_3$ | —CH(CH$_3$)CH$_2$OCH$_3$ | Cl | Cl | 2 | 160 | 44 |
| 6 | —CH$_2$CH$_2$OCH$_3$ | —CH(CH$_3$)$_2$ | Cl | Cl | 1 | 132 | 31 |
| 7 | —CH$_2$CH$_2$OCH$_2$CH$_3$ | —CH$_2$CH$_3$ | Cl | Cl | 1 | 118 | 44 |
| 8 | —CH$_3$ | —C(CH$_3$)$_2$CH$_2$OCH$_3$ | Cl | Cl | 1 | 120 | 17 |
| 9 | —CH$_3$ | —CH$_2$C(CH$_3$)=CH$_2$ | Cl | Cl | 1 | 152 | 26 |
| 10 | —CH$_3$ | —C$_2$H$_5$ | Cl | —CH$_3$ | | 150 | 18 |

EXAMPLE 11 (method c[1], c[2])

5.74 g of 2,3-dichlorobenzylideneacetylacetic acid methylester, 2.6 g of ethylacetoacetate and 2.8 mls of conc. NH$_3$ were dissolved in 25 mls tert.-butanol. The reaction mixture was allowed to stand at ambient temperature for 5 days, whereupon the tert.-butanol was evaporated and the residue was dissolved in isopropylether. After cooling the compound crystallized and after recrystallization from isopropylether pure 2,6-dimethyl-4-(2,3-dichlorophenyl)-1,4-dihydropyridine-3,5-dicarboxylic acid-3-methylester-5-ethylester was obtained, M.p. 145° C. Yield 59%.

EXAMPLE 12 (method d)

10.7 g of 2-bromo-3-chlorobenzaldehyde, 6.3 g of ethylacetoacetate, 5.7 g of methylacetoacetate and 5 mls of conc. NH$_3$ were dissolved in 25 mls of ethanol. The reaction mixture was refluxed over night, whereupon it was poured out onto ice-water. Thereby the compound crystallized and after recrystallization from ethanol pure 2,6-dimethyl-4-(2-bromo-3-chlorophenyl)-1,4-dihydropyridine-3,5-dicarboxylic acid-3-methylester-5-ethylester was obtained. M.p. 159° C. Yield 48%.

EXAMPLE 13

A syrup containing 2% (weight per volume) of active substance was prepared from the following ingredients:

| | | |
|---|---|---|
| 2,6-dimethyl-4-(2,3-chlorophenyl)-1,4-dihydropyridine-3,5-dicarboxylic acid-3-methylester-5-ethylester | | 2.0 g |
| Saccharine | | 0.6 g |
| Sugar | | 30.0 g |
| Glycerine | | 5.0 g |
| Flavouring agent | | 0.1 g |
| Ethanol 96% | | 10.0 g |
| Distilled water | ad | 100.0 ml |

Sugar, saccharine and the active substance were dissolved in 60 g of warm water. After cooling, glycerine and solution of flavouring agents dissolved in ethanol were added. To the mixture water was then added to 100 ml.

The above named active substance may be replaced by other therapeutically active substances of the invention.

EXAMPLE 14

Granules were prepared from 2,6-dimethyl-4-(2,3-dichlorophenyl)-1,4-dihydropyridine-3,5-dicarboxylic acid-3-methylester-5-(1-methyl-2-methoxyethyl)ester (250 g), lactose (175.9 g) and an alcoholic solution of polyvinylpyrrolidone (25 g). After the drying step the granules were mixed with talc (25 g), potatoe starch (40 g) and magnesium stearate (2.50 g) and were pressed into 10.000 tablets being biconvex. These tablets are coated with a 10% alcoholic solution of shellac and thereupon with an aqueous solution containing saccharose (45%), gum arabicum (5%), gelatine (4%) and dyestuff-(0.2%). After the first five coatings talc and powdered sugar were used for powdering. The priming coat was then coated with a 66% sugar syrup and polished with a 10% carnauba wax solution in carbon tetrachloride.

BIOLOGICAL TESTS

The antihypertensive effect of the compounds was tested in conscious, unrestrained spontaneously hypertensive rats (SHR) of the Okamoto strain. The animals had been prepared by prior implantation of indwelling catheters in the abdominal aorta via the femoral artery. Mean arterial blood pressure (MABP) and heart rate were continuously monitored. After a 2 hour control period the compound under study was administered by oral intubation at 2 hour intervals, suspended in methocel solution (5 ml/kg bodyweight). The cumulated doses were 1, 5 and 25 μmoles/kg bodyweight. The antihypertensive response, i.e. the BP reduction to each dose, was expressed as a percentage of the initial control BP level and plotted against the dose on a logarithmic scale. The dose which would give 20 percent BP reduction was then determined by interpolation. The results are shown in table 2.

The specificity towards smooth muscle relaxation was examined as follows: The isolated portal vein preparation of Wistar rats was mounted in an organ bath together with a paced isolated papillary heart muscle preparation of the same animal. The integrated contractile activity of the portal vein smooth muscle and the peak force amplitude of the papillary, myocardial, preparation were recorded. The respective activities during a 30 min control period were set as 100 percent and the ensuing activities under the influence of an agent under study were expressed as a percentage thereof. The agent was administered at 10 min intervals and the potency for vasodilatation(-log $ED_{50}$ of portal vein) and that of myocardial depression (-log $ED_{50}$ of papillary muscle) were determined by interpolation from the concentration-effect relationships determined in each experiment. A "separation" value was determined for each compound by averaging the differences of the -log $ED_{50}$ values for vasodilatation and myocardial depression, respectively, obtained in the experiments. This logarithmic separation value was transformed into numeric format and entered into table 2.

The compounds of the invention were compared with Nifedipin [2,6-dimethyl-4-(2-nitrophenyl)-1,4-dihydropyridine-3,5-dicarboxylic acid-3,5-dimethylester].

TABLE 2

| Compound according to Ex. | SHR $ED_{20}$ μmoles/kg bodyweight | Ratio heart vasc. |
| --- | --- | --- |
| 1 | 4 | 98 |
| 2 | 15 | 78 |
| 3 | 1 | 56 |
| 5 | 7 | 124 |
| 4 | 5 | 48 |
| 9 | 2 | 44 |
| 7 | — | 28 |
| 6 | 4 | 107 |
| Nifedipin | 5 | 15 |
| 8 | 8 | 118 |

We claim:

1. A compound of the formula I

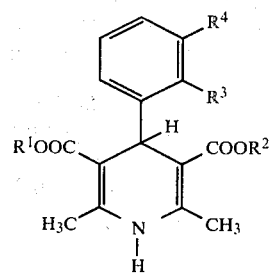

wherein $R^1$ is selected from the group consisting of —$CH_3$, —$C_2H_5$, —$CH_2CH_2OCH_3$, and —$CH_2CH_2OC_2H_5$, $R^2$ is selected from the group consisting of —$CH_2CH_3$, —$CH(CH_3)_2$, —$C(CH_3)_3$, —$CH(CH_3)CH_2OCH_3$, —$C(CH_3)_2CH_2OCH_3$, and —$CH_2C(CH_3)$=$CH_2$, whereby $R^1$ and $R^2$ are not the same, $R^3$ is chloro and $R^4$ is selected from the group consisting of chloro, and methyl.

2. A compound of claim 1, wherein $R^1$ is selected from the group consisting of —$CH_3$, —$CH_2CH_2OCH_3$, and —$CH_2CH_2OC_2H_5$, and $R^2$ is selected from the group consisting of —$C_2H_5$, —$CH(CH_3)_2$, —$C(CH_3)_3$, —$CH(CH_3)CH_2OCH_3$, and $C(CH_3)_2CH_2OCH_3$, $R^3$ is chloro, and $R^4$ is selected from the group consisting of chloro, and methyl.

3. A compound of claim 1, wherein $R^1$ is —$CH_3$, —$C_2H_5$, —$CH_2CH_2OCH_3$, and —$CH_2CH_2OC_2H_5$, $R^2$ is —$CH_2C(CH_3)$=$CH_2$, $R^3$ is chloro, and $R^4$ is selected from the group consisting of chloro, and methyl.

4. A method for treating arterial hypertension in a mammal suffering therefrom, comprising administering to said mammal an amount effective to relax the vascular smooth muscle of said mammal of a compound of formula I

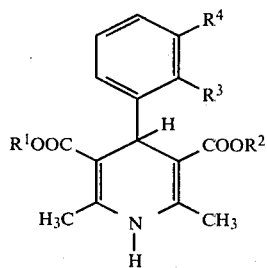

wherein $R^1$ is selected from the group consisting of —$CH_3$, —$C_2H_5$, —$CH_2CH_2OCH_3$, and —$CH_2CH_2OCH_2H_5$, $R^2$ is selected from the group consisting of —$CH_2CH_3$, —$CH(CH_3)_2$, —$C(CH_3)_3$, —$CH(CH_3)CH_2OCH_3$, —$C(CH_3)_2CH_2OCH_3$, and —$CH_2C(CH_3)$=$CH_2$, whereby $R^1$ and $R^2$ are not the same, $R^3$ is chloro, and $R^4$ is selected from the group consisting of chloro, and methyl.

5. A method according to claim 4, wherein a compound of formula I is administered, wherein $R^1$ is selected from the group consisting of —$CH_3$, —$CH_2CH_2OCH_3$, and —$CH_2CH_2OC_2H_5$, and $R^2$ is selected from the group consisting of —$C_2H_5$, —$CH(CH_3)_2$, —$C(CH_3)_3$, —$CH(CH_3)CH_2OCH_3$, and $C(CH_3)_2CH_2OCH_3$, $R^3$ is chloro and $R^4$ is selected from the group consisting of chloro, and methyl.

6. A method according to claim 4, wherein a compound of formula I is administered, wherein $R^1$ is —CH₃, —C₂H₅, —CH₂CH₂OCH₃, and —CH₂CH₂OC₂H₅, R² is selected from the group consisting of —CH₂C≡CH, —CH₂C(CH₃)=CH₂, R³ is chloro and methoxy, and R⁴ is selected from the group consisting of chloro, and methyl.

7. Pharmaceutical preparation, which comprises as an active ingredient a therapeutically effective dose of an antihypertensive compound having vascular smooth muscle relaxing properties which compound has the formula I

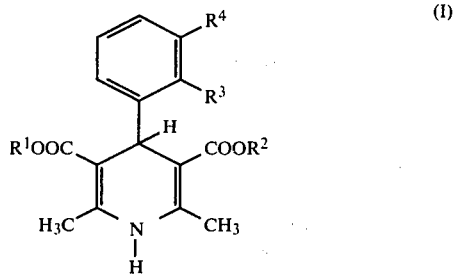

wherein R¹ is selected from the group consisting of —CH₃, —C₂H₅, —CH₂CH₂OCH₃, and —CH₂CH₂OC₂H₅, R² is selected from the group consisting of —CH₂CH₃, —CH(CH₃)₂, —C(CH₃)₃, —CH(CH₃)CH₂OCH₃, —C(CH₃)₂CH₂OCH₃, and —CH₂C(CH₃)=CH₂, whereby R¹ and R² are not the same, R³ is chloro, and R⁴ is selected from the group consisting of chloro, and methyl, in association with a pharmaceutically acceptable carrier.

8. A pharmaceutical preparation according to claim 7, wherein the active ingredient is a compound of formula I, wherein R¹ is selected from the group consisting of —CH₃, —CH₂CH₂OCH₃, and —CH₂CH₂OC₂H₅, and R² is selected from the group consisting of —C₂H₅, —CH(CH₃)₂, —C(CH₃)₃, —CH(CH₃)C₂H₅, —CH(CH₃)CH₂OCH₃, and C(CH₃)₂CH₂OCH₃, R³ is chloro and R⁴ is selected from the group consisting of chloro and methyl.

9. A pharmaceutical preparation according to claim 7, wherein the active ingredient is a compound of formula I, wherein R¹ is —CH₃, —C₂H₅, —CH₂CH₂OCH₃, and —CH₂CH₂OC₂H₅, R² is selected from the group consisting of —CH₂C(CH₃)=CH₂, R³ is chloro, and R⁴ is selected from the group consisting of chloro, and methyl.

10. A pharmaceutical preparation according to claim 7, wherein the substituted 2,6-dimethyl-4-phenyl-1,4-dihydropyridine-3,5-dicarboxylic acid-diester compound comprises 0.1 to 99% by weight of the preparation.

11. The compound according to claim 1 which is 2,6-dimethyl-4-(2,3-dichlorophenyl)-1,4-dihydropyridine-3,5-dicarboxylic acid-3-methylester-5-ethylester.

12. The compound according to claim 1 which is 2,6-dimethyl-4-(2,3-dichlorophenyl)-1,4-dihydropyridine-3,5-dicarboxylic acid-3-ethylester-5-(2-methoxyethylester).

13. The compound according to claim 1 which is 2,6-dimethyl-4-(2,3-dichlorophenyl)-1,4-dihydropyridine-3,5-dicarboxylic acid-3-methylester-5-isopropylester.

14. The compound according to claim 1 which is 2,6-dimethyl-4-(2,3-dichlorophenyl)-1,4-dihydropyridine-3,5-dicarboxylic acid-3-methyl-5-tert.butylester.

15. The compound according to claim 1 which is 2,6-dimethyl-4-(2,3-dichlorophenyl)-1,4-dihydropyridine-3,5-dicarboxylic acid-3-methylester-5-(2-methoxy-1-methylethylester).

16. The compound according to claim 1 which is 2,6-dimethyl-4-(2,3-dichlorophenyl)-1,4-dihydropyridine-3,5-dicarboxylic acid-3-(2-methoxyethyl)ester-5-isopropylester.

17. The compound according to claim 1 which is 2,6-dimethyl-4-(2,3-dichlorophenyl)-1,4-dihydropyridine-3,5-dicarboxylic acid-3-(2-ethoxyethyl)ester-5-ethylester.

18. The compound according to claim 1 which is 2,6-dimethyl-4-(2,3-dichlorophenyl)-1,4-dihydropyridine-3,5-dicarboxylic acid-3-methylester-5-(2-methoxy-1,1-dimethylethyl)ester.

19. The compound according to claim 1 which is 2,6-dimethyl-4-(2,3-dichlorophenyl)-1,4-dihydropyridine-3,5-dicarboxylic acid-3-(2-methoxy)ethylester-5-propargyl ester.

20. The compound according to claim 1 which is 2,6-dimethyl-4-(2,3-dichlorophenyl)-1,4-dihydropyridine-3,5-dicarboxylic acid-3-methylester-5-(2-methyl)allylester.

21. A pharmaceutical preparation according to claim 7 wherein said active ingredient is the compound 2,6-dimethyl-4-(2,3-dichlorophenyl)-1,4-dihydropyridine-3,5-dicarboxylic acid-3-methylester-5-ethylester.

22. A pharmaceutical preparation according to claim 7 wherein said active ingredient is the compound 2,6-dimethyl-4-(2,3-dichlorophenyl)-1,4-dihydropyridine-3,5-dicarboxylic acid-3-ethylester-5-(2-methoxyethylester).

23. A pharmaceutical preparation according to claim 7 wherein said active ingredient is the compound 2,6-dimethyl-4-(2,3-dichlorophenyl)-1,4-dihydropyridine-3,5-dicarboxylic acid-3-methylester-5-isopropylester.

24. A pharmaceutical preparation according to claim 7 wherein said active ingredient is the compound 2,6-dimethyl-4-(2,3-dichlorophenyl)-1,4-dihydropyridine-3,5-dicarboxylic acid-3-methyl-5-tert.butylester.

25. A pharmaceutical preparation according to claim 7 wherein said active ingredient is the compound 2,6-dimethyl-4-(2,3-dichlorophenyl)-1,4-dihydropyridine-3,5-dicarboxylic acid-3-methylester-5-(2-methoxy-1-methylethylester).

26. A pharmaceutical preparation according to claim 7 wherein said active ingredient is the compound 2,6-dimethyl-4-(2,3-dichlorophenyl)-1,4-dihydropyridine-3,5-dicarboxylic acid-3-(2-methoxyethyl)ester-5-isopropylester.

27. A pharmaceutical preparation according to claim 7 wherein said active ingredient is the compound 2,6-dimethyl-4-(2,3-dichlorophenyl)-1,4-dihydropyridine-3,5-dicarboxylic acid-3-(2-ethoxyethyl)ester-5-ethylester.

28. A pharmaceutical preparation according to claim 7 wherein said active ingredient is the compound 2,6-dimethyl-4-(2,3-dichlorophenyl)-1,4-dihydropyridine-3,5-dicarboxylic acid-3-methylester-5-(2-methoxy-1,1-dimethylethyl)ester.

29. A pharmaceutical preparation according to claim 7 wherein said active ingredient is the compound 2,6-dimethyl-4-(2,3-dichlorophenyl)-1,4-dihydropyridine-3,5-dicarboxylic acid-3-(2-methoxy)ethylester-5-propargyl ester.

30. A pharmaceutical preparation according to claim 7 wherein said active ingredient is the compound 2,6-dimethyl-4-(2,3-dichlorophenyl)-1,4-dihydropyridine-3,5-dicarboxylic acid-3-methylester-5-(2-methyl)allylester.

* * * * *

UNITED STATES PATENT AND TRADEMARK OFFICE
CERTIFICATE OF CORRECTION

PATENT NO. : 4,264,611

DATED : April 28, 1981

INVENTOR(S) : Berntsson et al.

It is certified that error appears in the above—identified patent and that said Letters Patent is hereby corrected as shown below:

First page, Item 75, after "Ljung" insert --Göteborg--;

First page, 2nd col., 6th from bottom line of ABSTRACT, after "$R^3$ is," delete "selected from the group consisting of";

Col. 2, line 39, ")1,4" should read --)-1,4--;

Col. 3, line 20, "(wherein" should read --wherein--;

Col. 7, line 35, "3,51" should read --3,5--;

IN THE CLAIMS:

Col. 11, lines 3 & 4, delete "and methoxy";

Col. 11, line 37, delete "-CH($CH_3$)$C_2H_5$,".

Signed and Sealed this

First Day of September 1981

[SEAL]

Attest:

GERALD J. MOSSINGHOFF

Attesting Officer       Commissioner of Patents and Trademarks

UNITED STATES PATENT AND TRADEMARK OFFICE

CERTIFICATE EXTENDING PATENT TERM
UNDER 35 U.S.C. § 156

PATENT NO.: 4,264,611

DATED: April 28, 1981

INVENTORS: Peder B. Berntsson et al.

PATENT OWNER: Aktiebolaget Astra

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

2 YEARS with all rights pertaining thereto as provided by 35 U.S.C. § 156(b).

I have caused the seal of the Patent and Trademark Office to be affixed this 20th day of May 1993.

Michael K. Kirk
Acting Commissioner of Patents and Trademarks

REEXAMINATION CERTIFICATE (221st)
United States Patent [19]
Berntsson et al.

[11] B1 4,264,611
[45] Certificate Issued Jul. 17, 1984

[54] 2,6-DIMETHYL-4-2,3-DISUBSTITUTED PHENYL-1,4-DIHYDRO-PYRIDINE-3,5-DICARBOXYLIC ACID-3,5-ASYMMETRIC DIESTERS HAVING HYPOTENSIVE PROPERTIES, AS WELL AS METHOD FOR TREATING HYPERTENSIVE CONDITIONS AND PHARMACEUTICAL PREPARATIONS CONTAINING SAME

[75] Inventors: Peder B. Berntsson, Mölndal; Stig A. I. Carlsson, Mölnlycke; Jan Ö Gaarder, Göteborg; Bengt R. Ljung, all of Sweden

[73] Assignee: Aktiebolaget Hassle, Mölndal, Sweden

Reexamination Request:
No. 90/000,413, Jun. 30, 1983

Reexamination Certificate for:
Patent No.: 4,264,611
Issued: Apr. 28, 1981
Appl. No.: 50,083
Filed: Jun. 19, 1979

[30] Foreign Application Priority Data

Jun. 30, 1978 [SE] Sweden .............................. 7807404

[51] Int. Cl.³ .................. C07D 213/55; A61K 31/455
[52] U.S. Cl. .................................... 424/266; 546/321
[58] Field of Search ........................ 546/321; 424/266

[56] References Cited
FOREIGN PATENT DOCUMENTS
2117573 10/1972 Fed. Rep. of Germany ...... 546/321

*Primary Examiner*—Alan L. Rotman

[57] ABSTRACT

The present invention relates to new compounds having antihypertensive effect, which compounds are of the formula I,

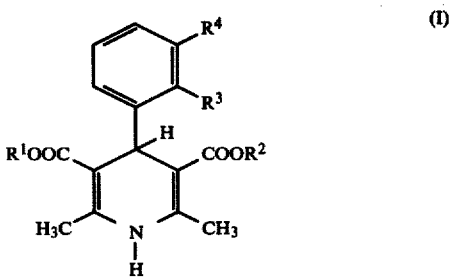

wherein $R^1$ is selected from the group consisting of $-CH_3$, $-C_2H_5$, $-CH_2CH_2OCH_3$, and $-CH_2CH_2OC_2H_5$, and $R^2$ is selected from the group consisting of $-C_2H_5$, $-CH(CH_3)_2$, $-C(CH_3)_3$, $-CH(CH_3)CH_2OCH_3$, $C(CH_3)_2CH_2OCH_3$, and $-CH_2C(CH_3)=CH_2$, whereby $R^1$ and $R^2$ are not the same, $R^3$ is selected from the group consisting of chloro, and $R^4$ is selected from the group consisting of chloro, and methyl, a method for lowering the blood pressure in mammals including man using said compounds, and pharmaceutical preparations containing said compounds.

REEXAMINATION CERTIFICATE ISSUED UNDER 35 U.S.C. 307.

NO AMENDMENTS HAVE BEEN MADE TO THE PATENT.

AS A RESULT OF REEXAMINATION, IT HAS BEEN DETERMINED THAT:

The patentability of claims 1-30 is confirmed.

* * * * *